United States Patent
Sharma et al.

(10) Patent No.: US 11,123,358 B2
(45) Date of Patent: Sep. 21, 2021

(54) MEDICAMENT FOR THE TREATMENT OF ACUTE LIVER FAILURE

(71) Applicant: MEDIZINISCHE HOCHSCHULE HANNOVER, Hannover (DE)

(72) Inventors: Amar Sharma, Hannover (DE); Michael Ott, Hannover (DE); Tobias Cantz, Hannover (DE); Dakai Yang, Hannover (DE)

(73) Assignee: Medizinische Hochschule Hannover, Hannover (DE)

( * ) Notice: Subject to any disclaimer, the term of this patent is extended or adjusted under 35 U.S.C. 154(b) by 0 days.

(21) Appl. No.: 16/302,502

(22) PCT Filed: May 30, 2017

(86) PCT No.: PCT/EP2017/062997
§ 371 (c)(1),
(2) Date: Nov. 16, 2018

(87) PCT Pub. No.: WO2017/211617
PCT Pub. Date: Dec. 14, 2017

(65) Prior Publication Data
US 2019/0167713 A1    Jun. 6, 2019

(30) Foreign Application Priority Data

Jun. 6, 2016  (EP) .................. 16173158.3

(51) Int. Cl.
*C12N 15/11* (2006.01)
*A61K 31/7105* (2006.01)
*A61K 31/713* (2006.01)
*A61P 39/00* (2006.01)
*A61P 1/16* (2006.01)
*A61K 48/00* (2006.01)

(52) U.S. Cl.
CPC ........ *A61K 31/7105* (2013.01); *A61K 31/713* (2013.01); *A61K 48/0066* (2013.01); *A61K 48/0075* (2013.01); *A61K 48/0083* (2013.01); *A61P 1/16* (2018.01); *A61P 39/00* (2018.01)

(58) Field of Classification Search
CPC .............................. A61K 31/7105; A61P 1/16
See application file for complete search history.

(56) References Cited

U.S. PATENT DOCUMENTS

2012/0264805 A1    10/2012    Sharma et al.

FOREIGN PATENT DOCUMENTS

| EP | 2123579 B1 | 11/2009 | |
|---|---|---|---|
| EP | 2203559 B1 | 7/2010 | |
| EP | 2205737 B1 | 7/2010 | |
| EP | 2261334 B1 | 12/2010 | |
| EP | 2123759 B1 | 2/2014 | |
| EP | 2757157 A1 | 7/2014 | |
| WO | WO-2014111876 A2 * | 7/2014 | ........... A61K 31/713 |

OTHER PUBLICATIONS

Tomar et al, 3,3'-Diindolylmethane attenuates LPS-mediated acute liver failure by regulating miRNAs to target, British Journal of Pharmacology, Dec. 2014, 172: 2133-2147 (Year: 2014).*
Ward et al., "Circulating MicroRNA Profiles in Human Patients with Acetaminophen Hepatotoxicity or Ischemic Hepatitis", Proc Natl Acad Sci USA 111, 12169-12174 (2014).
Sharma et al., "MicroRNA Regulates FAS-Induced Fulminant Liver Failure", Hepatology 53, 1651-1661 (2011).
Yang et al., "MicroRNA-125b-5p Mimic Inhibits Acute Liver Failure", Nature Communications, 1-11 (2016).
John et al., "MicroRNAs Play a Role in Spontaneous Recovery From Acute Liver Failure", Hepatology 60, 1346-1355 (2014).
Ninomiya et al., "The Expression of MiR-125B-5p is Increased in the Serum of Patients with Chronic Hepatitis B Infection and Inhibits the Detection of Hepatitis B Virus Surface Antigen", Journal of Viral Hepatitis 23, 330-339 (2016).
Hubner, Werner, International Search Report for Application No. PCT/EP2017/062997, dated Aug. 25, 2017.

* cited by examiner

*Primary Examiner* — Ekaterina Poliakova-Georgantas
(74) *Attorney, Agent, or Firm* — Greer, Burns & Crain, Ltd.; Steven P. Fallon (57) ABSTRACT

The present invention relates to a compound for use as a medicament in the treatment or prevention of acute liver failure, which acute liver failure is induced by intoxication prior to or following administration of the compound. Accordingly, the invention relates to the compound for use in the treatment of an intoxication that without treatment is expected to result in acute liver failure or that without treatment is sufficient to induce acute liver failure. The invention also provides the compound for use in the treatment, and a corresponding method for the treatment of an intoxication sufficient to induce acute liver failure.

6 Claims, 6 Drawing Sheets

Specification includes a Sequence Listing.

MEDICAMENT FOR THE TREATMENT OF ACUTE LIVER FAILURE

The present invention relates to a compound for use as a medicament in the treatment or prevention of acute liver failure, which acute liver failure is e.g. induced by intoxication prior to or following administration of the compound. Accordingly, the invention relates to the compound for use in the treatment of an intoxication that without treatment is expected to result in acute liver failure or that without treatment is sufficient to induce acute liver failure. The invention also provides the compound for use in the treatment, and a corresponding method for the treatment of an intoxication sufficient to induce acute liver failure. The compound is preferably administered within at maximum 4 days following the intoxication in order to prevent acute liver failure caused by the intoxication. The compound can be formulated as a pharmaceutical composition, preferably for i.v. injection, e.g. as a solution, preferably as an aqueous solution, as liposomes and/or as a cholesterol ester and/or as nanoparticles, e.g with a carrier.

Administration of the compound has been shown to significantly protect against acute liver failure artificially induced by a previous injection of a paracetamol overdose or injection of FAS agonist antibody sufficient to induce apoptosis. The compound is suitable for i.v. injection and has shown significant activity in preventing or protecting against the acute liver failure that in the absence of the compound can be expected to be caused by the intoxication, e.g. presence of toxic agents like non-viral toxic agents or virus.

STATE OF THE ART

US 2012/0264805 describes a number of siRNA molecules hybridising to the mRNA encoding the p53 upregulated modulator of apoptosis (PUMA) for reducing or preventing expression of PUMA in the treatment of a functionally impaired liver and for prevention of acute liver failure. The treatments quoted as known for treatment of acute liver failure include an antiviral therapy in the case of virally induced liver failure and the administration of a chemical antidote in drug abuse, e.g. of acetylcysteine in the case of paracetamol intoxication.

Ward et al., Proc Natl Acad Sci USA 111, 12169-12174 (2014) describe elevated serum levels inter alia of miR-125b-5p in patients with acetaminophen (paracetamol) hepatotoxicity or ischemic hepatitis.

EP2 261 334 B1 describes stabilized RNA molecules having a phosphorylation of the 5" nucleotide at its 5" carbon and/or an O-alkylation of the 2' carbon of the at least one of the three 5"-terminal nucleotides.

EP 2 123 579 B1 describes stabilized RNA molecules having a 2"-O-alkyl modification of the two 5"-terminal nucleotides and a 2"-O-alkyl modification of at least one pyrimidine.

Sharma et al., Hepatology 53, 1651-1661 (2011) describe that microRNA-221 regulates FAS-induced fulminant liver failure.

EP 2 203 559 B1 describes an antisense oligonucleotide to inhibit miR-122 in the treatment of HCV, which antisense oligonucleotide is locked nucleic acid.

EP 2 205 737 B1 describes oligomers having 7-10 nucleobases which are locked nucleic acids.

OBJECT OF THE INVENTION

It is an object of the invention to provide a compound for use in preventing or at least significantly reducing acute liver failure, preferably in acute liver failure that can be expected due to presence of toxic agents.

DESCRIPTION OF THE INVENTION

The invention achieves the object by the features of the claims and especially by providing a compound having the nucleobase sequence of miR-125b-5p (UCCCUGAGACCCUAACUUGUGA, SEQ ID NO: 1) for use in the treatment of intoxication sufficient to cause acute liver failure. The compound miR-125b-5p preferably is contained in a pharmaceutically acceptable formulation for injection, e.g. for i.v. injection. The formulation can e.g. be a liposome preparation containing the compound, a chemical modification, e.g. by attached cholesterol esters, conjugating miR-125b-5p mimic with nanoparticles, or using adeno-associated vectors or a combination of at least two of these. Herein, reference to a miRNA refers to the functional miRNA molecule of 21 to 22 nt, usually 22 nt, which in a cell is generated from a precursor miRNA, usually having 66 nt, that is the transcription product of a primary miRNA.

The compound miR-125b-5p can be chemically modified e.g. for enhanced stability in blood, e.g. as known in the state of art, for example in the form of locked nucleic acid, by phosphorylation of the 5'-terminal nucleotide at its 5' carbon and/or an O-alkylation of the 2' carbon of the at least one of the three 5'-terminal nucleotides, a 2'-O-alkyl modification of the two 5'-terminal nucleotides and a 2'-O-alkyl modification of at least one pyrimidine, or in the form of peptide nucleic acid, or a combination of at least two of these, wherein the compound has the nucleobase sequence of SEQ ID NO: 1. For a locked nucleic acid, the cytosine moieties can be 5'-methyl cytosine and all internucleoside bonds can be phosphorothioate bonds.

The use of the compound as a medicament has the advantage of directly reducing or preventing acute liver failure, as no transcription from a coding sequence is necessary following administration into the patient.

The compound is preferably formulated for administration to a patient within at maximum 4 days, also within at maximum 3 days, preferably within at maximum 2 days, more preferably within at maximum 1 day, most preferably within at maximum 12 to 6 h subsequent to the intoxication. Therein, the intoxication is sufficient to cause acute liver failure in the absence of a suitable treatment.

Intoxication which without treatment results in acute liver failure can e.g. be caused by a viral agent, e.g. hepatitis B virus and/or by presence of drugs, e.g. by drug abuse, the drug being e.g. selected from acetaminophen (paracetamol) and/or alcohol. Preferably, the compound is for use in the treatment of intoxication sufficient to cause acute liver failure, wherein the intoxication is caused by a synthetic or natural compound, e.g. acetaminophen, and preferably excluding virus infections, wherein further preferably the intoxication has occurred at maximum 4 days prior to the treatment, more preferably at maximum 3 days, 2 days or 1 day prior to the treatment.

For the purposes of the invention, acute liver failure includes fulminant and subfulminant liver failure and is for example characterized by depletion of glutathione, e.g. a lower serum glutathione to glutathione disulfide ratio (GSH/GSSG level), increased TUNEL positive cell nuclei, a higher serum level of alanine transaminase, a higher serum level of aspartate transaminase, an increased serum level of serum glutamate dehydrogenase, an increased serum mitochondrial DNA level and deteriorated liver morphology compared to respective parameters in an unaffected, e.g. healthy individual.

Preferably, acute liver failure for the purposes of the invention excludes liver cancer.

The examples show that the compound having the nucleobase sequence of miR-125b-5p can prevent acute liver failure when administered to a mammal, exemplified by mice, following intoxication sufficient to result in acute liver failure, e.g. an intoxication by a lethal dose of paracetamol or by a lethal dose of anti-CD95 antibody inducing apoptosis. In respect of paracetamol, the results obtained in mice are taken as a basis for extrapolating that in humans the administration of the compound at maximum 4 days, preferably at maximum 3 days, more preferably at maximum 2 days or 1 day following intoxication will reduce or prevent acute liver failure at least to a degree allowing survival.

The invention is now described by way of examples using paracetamol or FAS agonist antibody representing intoxication resulting in acute liver failure. Herein, and in the examples, the miRNA is also referred to as a mimic as it can be produced by synthesis. The mimic can optionally have a chemical modification. In the figures, data in the absence of a compound intended to counteract acute liver failure, e.g. caused by administration of paracetamol or by anti-CD95 antibody, are designated as Control, data generated in the absence of an intoxicating agent and in the absence of a compound intended to counteract acute liver failure are designated as Uninjured, and data generated in the presence of the preferred compound miR-125b-5p are designated miR-125b-5p mimic. *indicates $P<0.05$, two-tailed Student's t-test; **indicates $P<0.01$, two-tailed Student's t-test.

The examples make reference to the figures that show in

FIG. 1 the GSH/GSSG ratio in cultivated primary hepatocytes transfected with miRNAs with subsequent intoxication by paracetamol, FIG. 2 the GSH/GSSG ratio in cultivated primary hepatocytes transfected with inhibitors of miRNAs with subsequent intoxication by paracetamol, FIG. 3 the results of TUNEL assays in cultivated primary hepatocytes transfected with miRNAs or with inhibitors of miRNAs with subsequent induction of apoptosis by anti-CD95 antibody, FIG. 4 the relative expression of miR-125b-5p in virion transduced mice, FIG. 5 the survival of mice overexpressing miR-125b-5p following acute liver failure induced by paracetamol injection, FIG. 6 serum levels of AST (left columns) and ALT (right columns) for control and viral particle of the invention, FIG. 7 haematoxylin and eosin (HE) staining of liver tissue following acute liver failure induced by paracetamol injection, FIG. 8 analyses of serum GDH following acute liver failure induced by paracetamol injection, FIG. 9 analyses of serum GSH/GSSG ratios following acute liver failure induced by paracetamol injection, FIG. 10 analyses of serum mtDNA following acute liver failure induced by paracetamol injection, FIG. 11 relative expression levels of miR-125b-5p in mock-transduced mice and in mice transduced with a viral expression vector for miR-125b-5p, FIG. 12 Kaplan-Meier survival curves of mice overexpressing miR-125b-5p with subsequent FAS-induced apoptosis, FIG. 13 serum levels of AST (left columns) and ALT (right columns) for control and viral particle of the invention, FIG. 14 haematoxylin and eosin (HE) staining of liver tissue following acute liver failure induced by FAS-induced apoptosis, FIG. 15 relative Caspase-3/7 activities following acute liver failure induced by FAS-induced apoptosis, FIG. 16 TUNEL results following acute liver failure induced by FAS-induced apoptosis, FIG. 17 relative presence of miR-125b-5p in liver tissue of control mice (Control, no compound) and of mice having received injection of miR-125b-5p mimic, with previous i.p. injection of paracetamol, FIG. 18 Kaplan-Meier survival curves of mice having received injection of miR-125b-5p mimic or without compound (Control) with previous i.p. injection of paracetamol, FIG. 19 serum levels of AST (left columns) and ALT (right columns) in mice having received injection of miR-125b-5p mimic or without compound (Control) with previous i.p. injection of paracetamol, and in healthy mice (Uninjured), FIG. 20 haematoxylin and eosin (HE) staining of liver tissue with previous injection of paracetamol and subsequent injection of miR-125b-5p mimic or without compound (Control), FIG. 21 serum levels of GDH in mice having received injection of miR-125b-5p mimic or without compound (Control) with previous i.p. injection of paracetamol, FIG. 22 serum levels of GSH/GSSG in mice having received injection of miR-125b-5p mimic or without compound (Control) with previous i.p. injection of paracetamol, FIG. 23 serum levels of mtDNA in mice having received injection of miR-125b-5p mimic or without compound (Control) with previous i.p. injection of paracetamol, FIG. 24 relative presence of miR-125b-5p in liver tissue of control mice (Control, no compound) and of mice having received injection of miR-125b-5p mimic, with previous i.p. injection of anti-CD95 antibody, FIG. 25 Kaplan-Meier survival curves of mice having received injection of miR-125b-5p mimic or without compound (Control) with previous i.p. injection of anti-CD95 antibody, FIG. 26 serum levels of AST (left columns) and ALT (right columns) in mice having received injection of miR-125b-5p mimic or without compound (Control) with previous i.p. injection of anti-CD95 antibody, and in healthy mice (Uninjured), FIG. 27 haematoxylin and eosin (HE) staining of liver tissue in mice having received injection of miR-125b-5p mimic or without compound (Control) with previous i.p. injection of anti-CD95 antibody, FIG. 28 relative Caspase-3/7 activities of liver tissue in mice having received injection of miR-125b-5p mimic or without compound (Control) with previous i.p. injection of anti-CD95 antibody, and FIG. 29 TUNEL results of liver tissue in mice having received injection of miR-125b-5p mimic or without compound (Control) with previous i.p. injection of anti-CD95 antibody.

EXAMPLE 1

Screening of miRNAs for in Vitro Activity Against Acute Liver Failure Induced by Paracetamol Intoxication Hepatocytes were collected by low-speed centrifugation from Liberase (Roche) perfused and disintegrated mouse livers, discarding non-parenchymal cells with the supernatant. Hepatocytes were seeded at 10 000 cells per well cultivated in cell culture plates pre-coated with collagen (BD). In an unbiased screening, 302 different mimic miRNA molecules having sequences conserved between mouse and human and which have a chemical modification for increased stability against RNase, available as a mimic library (from Thermo Scientific, Germany), were added at 25 nM miRNA mimic to primary mouse hepatocytes for transfection after 12 h cultivation. Generally for transfection, Targefect reagent in the presence of virofect enhancer (obtained from Targeting Systems), cultivation was in Hepatocyte Culture Medium (obtained from Lonza). At 36 h after transfection, paracetamol was added to a final concentration of 3 mg/ml. In order to assess the effect of the miRNA on the toxicity induced by paracetamol or by the antibody, cell viability was measured by WST-1 assay (Roche) at 6 h after addition of the antibody or of paracetamol, absorbance was measured at 440 nm.

It was found that more than 20% protection against the toxic effect of paracetamol was obtained by the following seven miRNAs which in the normal human liver show a modest to high expression:

| miRNA | Cell viability (fold change) |
|---|---|
| miR-194-5p (SEQ ID NO: 2) | 1.57 |
| miR-125b-5p (SEQ ID NO: 1) | 1.45 |
| miR-21-5p (SEQ ID NO: 3) | 1.41 |
| let-7a-5p (SEQ ID NO: 4) | 1.38 |
| miR-122-5p (SEQ ID NO: 5) | 1.66 |
| miR-30c-5p (SEQ ID NO: 6) | 1.41 |
| miR 193a-3p (SEQ ID NO: 7) | 1.46 |

Change of cell viability was determined in relation to a control using scramble miRNA (obtained from Qiagen) replacing the miRNA mimic in the transfection.

As a control experiment, these miRNAs were inhibited by transfection of 25 nM reverse complimentary oligonucleotides into cultivated primary hepatocytes prior to addition of paracetamol. It was found that inhibition of let-7a, miR-125b-5p or of miR-122-5p resulted in lower cell viability compared to the scramble control. This shows that presence or absence of let-7a, miR-125b-5p or of miR-122-5p in hepatocytes correlates with protection against or lower cell viability in presence of the toxic agent in comparison to the scramble control.

Figure 1:
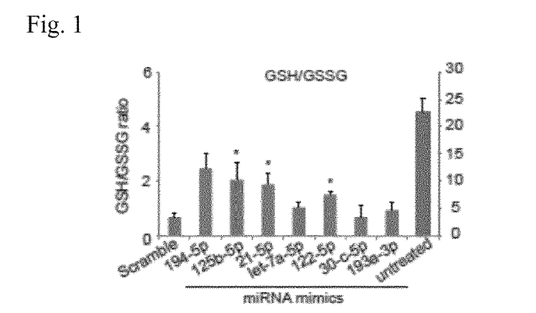
Figure 2:
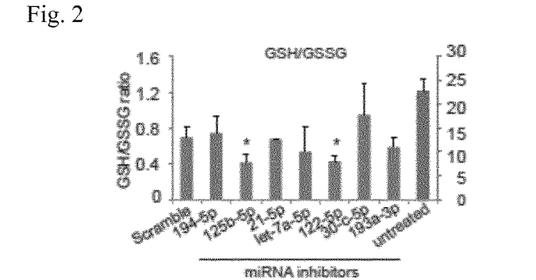

In cultivated primary hepatocytes transfected with one of the miRNAs miR-194-5p, miR-125b-5p, miR-21-5p, let-7a-5p, miR-122-5p, miR-30c-5p or miR 193a-3p, or their specific inhibitor, the ratio of glutathione to glutathione disulfide (GSH/GSSG ratio) was determined. The results are depicted in FIGS. 1 and 2, showing that in relation to scramble miRNA, the mimics of miR-125b-5p, of miR-194-5p, of miR-21-5p and of miR-122-5p each restored glutathione levels significantly, but only inhibitors of miR-125b-5p and of miR-122-5p led to a corresponding significant reduction of glutathione levels.

As glutathione depletion is one of the hallmarks of paracetamol-induced hepatotoxicity, these results indicate that administration of miR-125b-5p and of miR-122-5p protect against paracetamol-induced hepatocyte toxicity.

EXAMPLE 2

Screening of miRNAs for in Vitro Activity Against Acute Liver Failure Induced by FAS Agonist Antibody As a model for toxicity, FAS-induced apoptosis was used by administration of anti-CD95 antibody. Primary mouse hepatocytes were transfected by the set of 302 different mimic miRNA molecules as described in Example 1 and at 24 h post transfection, Hamster anti-mouse CD95 antibody (BD Pharmingen) was added to 1 µg/ml.

The FAS antibody causes massive apoptosis in vitro and in vivo, leading to acute liver failure. In this culture assay, the following mimics of miRNAs were found to reduce apoptosis:

| miRNA | Cell viability (fold change) |
|---|---|
| miR-130a-3p (SEQ ID NO: 8) | 1.36 |
| miR-125b-5p (SEQ ID NO: 1) | 1.32 |
| miR-29c-3p (SEQ ID NO: 9) | 1.29 |
| miR-16-5p (SEQ ID NO: 10) | 1.22 |
| miR-23-3p (SEQ ID NO: 11) | 1.38 |

These miRNA were selected for reducing apoptosis by at least 20% compared to scramble miRNA and for a modest to high expression in a normal liver.

These five mimics and their respective inhibitors were tested again for confirmation. It was found that only for miR-16-5p, the protective effect against apoptosis was not validated in the cell viability assay.

Figure 3:
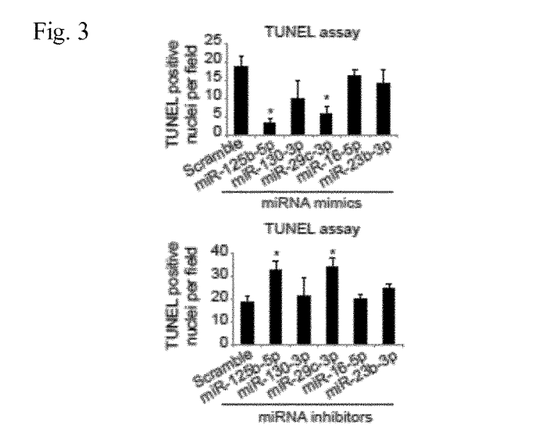

As a further assay, TUNEL (terminal deoxynucleotidyl transferase-mediated dUTP nick-end labelling) was analysed using TUNEL assay kit (obtained from Merck Millipore). The TUNEL assay confirmed protection against FAS-induced apoptosis of cultured hepatocytes by miR-125b-5p and by miR-29c-3p. The results of the TUNEL assay are shown in FIG. 3, depicting the number of TUNEL positive nuclei per microscope field for the indicated miRNAs.

As the assays of Example 1 and Example 2 both identified miR-125b-5p as the miRNA that protects primary hepatocytes in vitro against intoxication by paracetamol and against FAS-induced apoptosis, miR-125b-5p is the preferred compound for use in the treatment of acute liver failure.

For miR-125b-5p a dose dependent effect was found in primary hepatocyte culture for concentrations of at least 25 nM against paracetamol-induced or FAS-induced acute liver failure.

For cultivated human hepatocytes, FAS-antibody (mouse anti-human CD95 antibody, clone Dx2, BD Pharmingen) was added to 1µg/ml.

EXAMPLE 3

Figure 4:
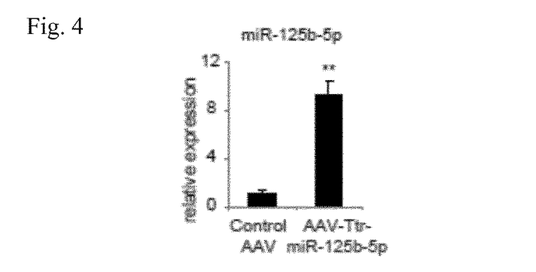

Use of miR-125b-5p Against Acute Liver Failure Induced by Paracetamol Intoxication In Vivo For testing the in vivo-effect of miR-125b-5p, male BALB/c mice were used. Mice were injected with adeno-associated viral (AAV) particles as generally described in Sharma et al., Hepatology (2011). The AAV plasmid contains the primary coding sequence pri-miR-125b-5p under the control of the hepatocyte specific transthyretin (Ttr) promoter for overexpression of miR-12b-5p. The virions containing this expression cassette for miR-12b-5p were prepared in high titer serotype 8, designated AAV-Ttr-miR-125b-5p. In short, A-293 cells were transfected with the transgene plasmid by Ca-phosphate transfection, and three days later cells were harvested and virions were purified by CsCl density gradient centrifugation. The titer was determined by reverse transcriptase PCR using primers spanning the Ttr promoter. For in vivo transduction, $1\times10^{10}$ virions were injected into the tail vein of 8 to 10 week old BALB/c mice once and $1\times10^{10}$ virions a second time 4 days later. Expression of miR-125b-5p in transduced mice was confirmed in relation to a control virion. FIG. 4 shows the relative expression of miR-125b-5p determined in mouse liver tissue. Expression of miRNA was determined from 50 ng total RNA isolated using the Taqman Universal Real Time PCR kit and SYBR green PCR master mix obtained from Applied Biosystems. For regular gene expression analyses data was normalized to β-actin (Actb) expression. Likewise, for miRNA expression analyses, data was normalized to expression of U6, small RNAs. Data were analysed according to the ΔΔCt method.

Figure 5:
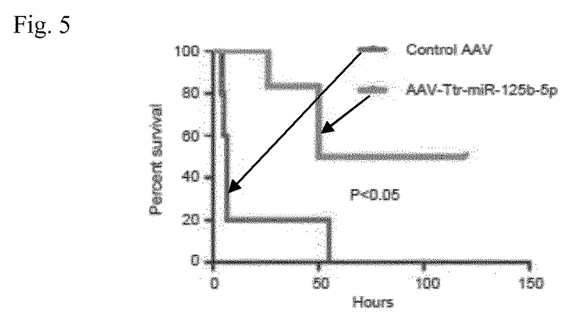

Three days following transduction, a portion of the transduced mice were injected intraperitoneally with 350 mg/kg paracetamol, a dose that was previously found to have 100% lethality in mice when testing doses from 150 to 800 mg/kg. The survival curves are shown in FIG. 5, indicating a significantly improved survival of mice expressing miR-125b-5p compared to mice that were transduced with a control virion with an empty expression cassette. The mice that had received the AAV-Ttr-miR-125b-5p and had survived the paracetamol were monitored for a further 6 months after induction of paracetamol toxicity. The long-term survival shows that overexpression of miR-125b-5p in the mouse liver generates resistance against acute liver failure induced by intoxication represented by a lethal dose of paracetamol.

In a further experiment, mice that were transduced to overexpress miR-125b-5p were injected i.p. with 350 mg/kg paracetamol as described above and killed 6 h later to examine serum levels of alanine transaminase (ALT) and of aspartate transaminase (AST), and histologically for hepatic injury. ALT and AST were analysed from 0.1 ml blood drawn from each mouse. After 30 min at room temperature, serum was prepared by centrifugation at 8000 ×g for 8 min, and the clear supernatant was analysed by a routine lab fully automated using an Olympus AU 400 analyser (Beckman Coulter).

Immunofluorescence and immunohistochemical staining for cleaved caspase-3 (obtained from Cell Signaling, catalogue No 9661, 1:400 dilution), cleaved caspase-7 (obtained from Cell Signaling, catalogue No 8438, 1:400 dilution) and Ki67 (obtained from Labvision, catalogue No.RM9106, 1:400 dilution) was performed on 10 μm cryosections from mouse liver tissue. In short, mouse liver lysates prepared by Dounce homogenisation in hypotonic extraction buffer containing Complete Mini Protease Inhibitor Cocktail (Roche) was centrifuged 15 min at 13000 rpm at 4° C., using 1 μg in a Caspase-Glo assay kit (obtained from Promega). For signal detection, AlexaFluor-conjugated secondary antibodies were used, measuring luminescence in a white 96 well plate. For haematoxylin and eosin (HE) staining, liver tissues were fixed in 4% formalin, embedded in paraffin and cut to 5 μm sections for histochemical analysis.

Figure 6:
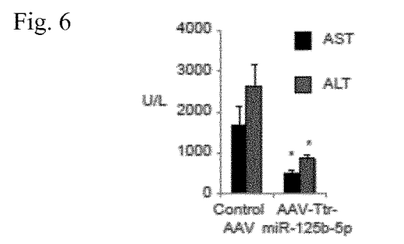
Figure 7:
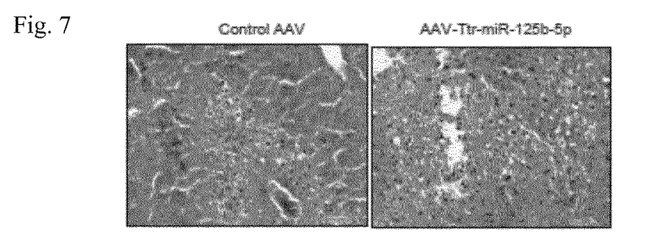

The results of ALT and AST analyses of FIG. 6 indicate lower serum levels of ALT and AST in serum of miR-125b-5p overexpressing mice, showing reduced liver damage at 6 h subsequent to paracetamol injection. The HE staining shown in FIG. 7 indicates reduced liver injury in miR-125b-5p overexpressing livers at 6 h after induction of acute liver failure by paracetamol injection.

Figure 8:
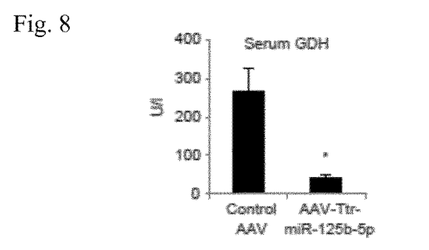
Figure 9:
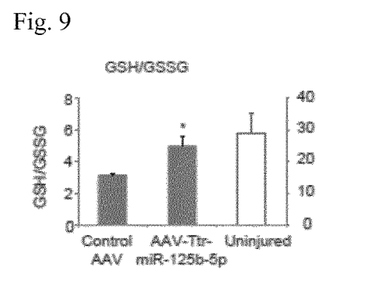
Figures 10, 11:
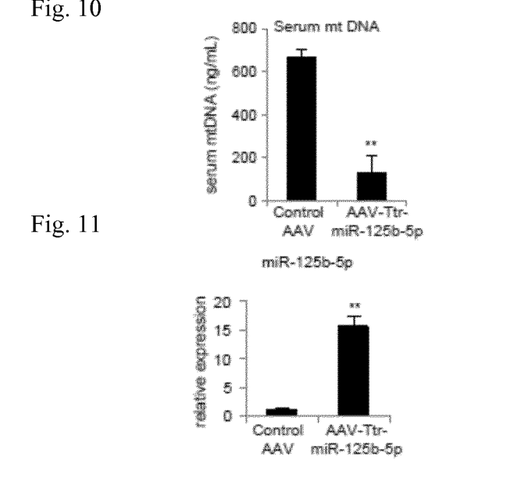

The analyses of serum glutamate dehydrogenase (GDH), the serum ratio of GSH/GSSG, and of serum mtDNA, shown in FIGS. 8, 9 and 10, confirm the protective effect of overexpression of miR-125b-5p against acute liver failure induced by paracetamol injection.

In FIG. 9, mice without injection of paracetamol (Uninjured) are shown as a control. GDH was measured using the GDH detection kit obtained from Abcam, using 5 μl serum diluted in assay buffer with colorimetric measurement at 450 nm. GSH and GSSG were measured using the GSH/GSSG Glo assay kit obtained from Promega on mouse liver homogenates in 5% w/v metaphosphoric acid (Sigma) and subsequently centrifuged at 13000 rpm for 10 min at 4° C., then neutralized and diluted. GSH and its oxidized form GSSG were measured by luminescence detection. Serum mtDNA was measured by quantitative real-time PCR on total DNA isolated from serum samples using a QIAamp Blood and Mini Kit (Qiagen). A standard curve was made for mtDNA of mouse liver tissue isolated from the Mitochondrial DNA Isolation kit (Abcam), purity of mtDNA was verified by real-time PCR for mouse cytochrome c oxidase subunit III and β-actin.

In the alternative to transduction of mice by two subsequent injections of $1\times10^{10}$ virions each time, $2\times10^{10}$ virions could be used in one injection for enhanced protection against intoxication. The analysis by staining Ki67 and quantification revealed that the protection against acute liver failure is due to suppression of cell death by miR-125b-5p, and that it is not due to increased proliferation of hepatocytes.

EXAMPLE 4

Use of miR-125b-5p Against FAS-Induced Acute Liver Failure In Vivo

Figure 12:
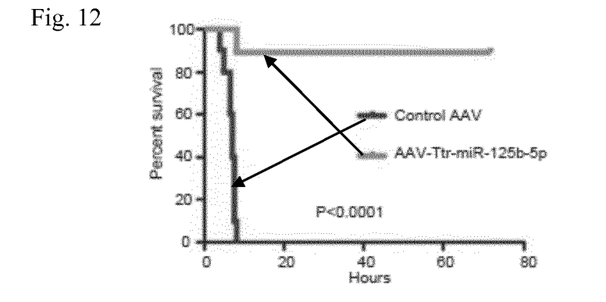
Figure 13:
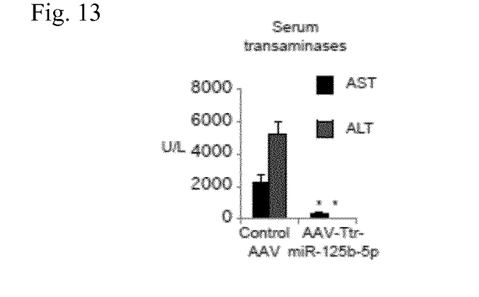
Figure 14:
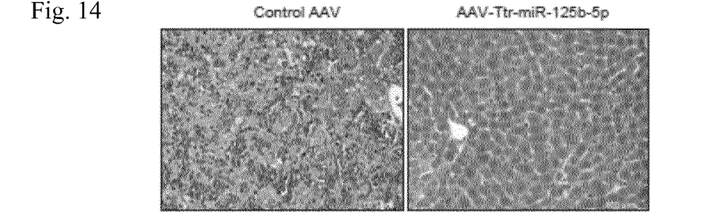
Figure 15:
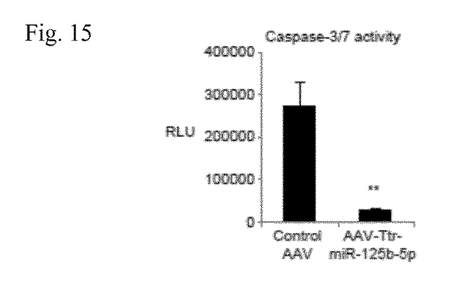
Figure 16:
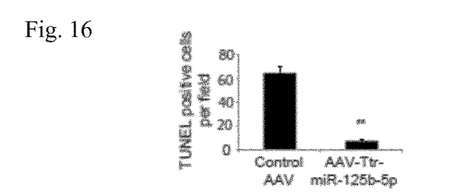

As a further example for an intoxication inducing acute liver failure, FAS-induced liver failure was analysed in BALB/c mice overexpressing miR-125b-5p. These mice were generated as described in Example 3 using 2 subsequent injections of $1\times10^{10}$ virions and were found to overexpress miR-125b-5p. At day 3 following the second injection of the AAV-Ttr-miR-125b-5p virion, a dose of FAS antibody was injected that was previously determined as lethal to mock-transduced (Control AAV) or native mice. The expression of miR-125b-5p is shown in FIG. 11 for mock-transduced mice (Control AAV), and for the mice transduced with AAV-Ttr-miR-125b-5p. The survival curve of FIG. 12 shows that the overexpression of miR-125b-5p significantly increases the survival rate at injection of an otherwise lethal FAS-induced apoptosis. Also the serum levels of AST and ALT depicted in FIG. 13, the HE staining of FIG. 14, the ratio of caspase-3 and caspase-7 activities of FIG. 15, and the TUNEL assay of FIG. 16 show significant protection against acute liver failure induced by the otherwise lethal dose of anti-CD95 antibody. This finding is supported by staining for cleaved caspase-3 and caspase-7.

EXAMPLE 5

Use of miR-125b-5p Against Paracetamol-Induced Acute Liver Failure In Vivo

As an example for the use of miR-125b-5p as a medicament in the treatment of acute liver failure that is expected in a patient due to previous intoxication, miR-125b-5p was administered to mice that had previously received a lethal dose of paracetamol.

Figure 17:
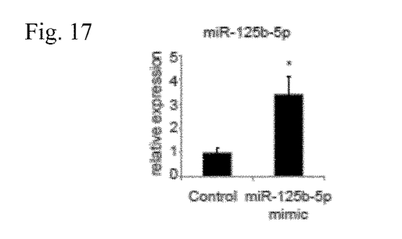
Figure 18:
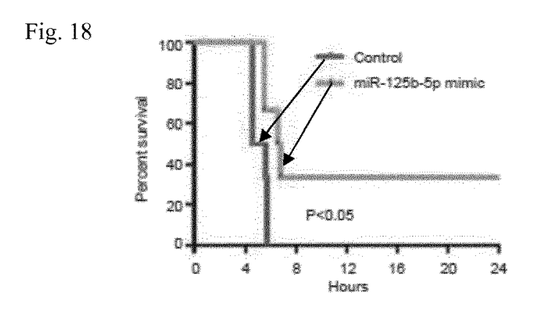

BALB/c mice were injected i.p. with 350 mg/kg paracetamol. 1 h later, the mice were injected into the tail vein with 10 μg miR-125b-5p in the form of stabilized RNA (miRIDIAN, obtained from GE Dharmacon). The analysis for the presence of miR-125b-5p in the liver of mice injected with this stabilized miR-125b-5p (miR-125b-5p mimic) compared to the level of miR-125b-5p in the liver of mice that received no miR-125b-5p is depicted in FIG. 17, showing a significantly increased presence of miR-125b-5p in the livers of mice that had received the stabilized miR-125b-5p mimic. The Kaplan-Meier survival curve of FIG. 18 shows the drastically improved survival in the mice that received the miR-125b-5p mimic following administration of the lethal dose of paracetamol.

Figure 19:
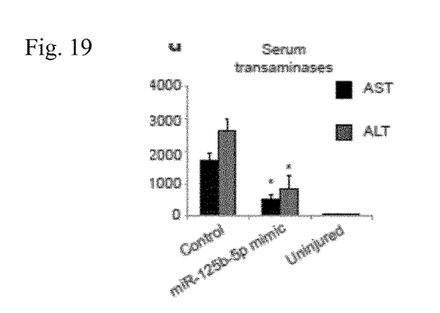
Figure 20:
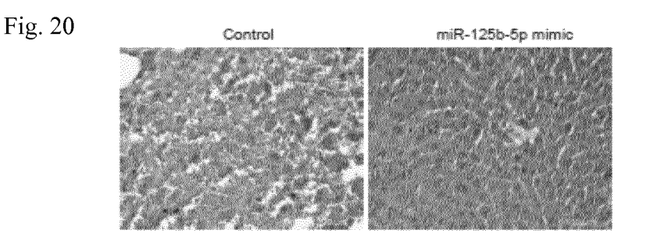
Figure 21:
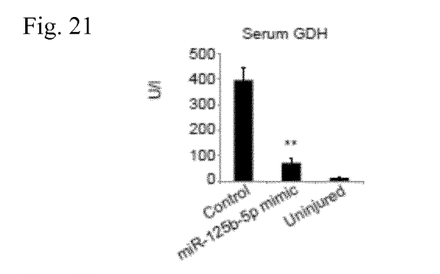
Figure 22:
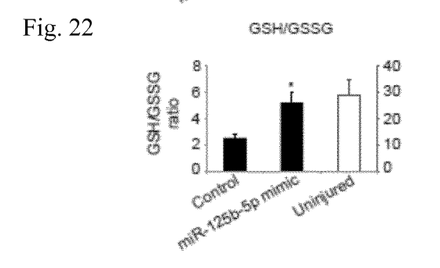
Figure 23:
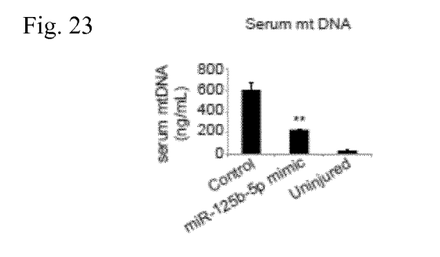

The analysis of serum levels of AST and ALT, results depicted in FIG. 19, show reduced AST and ALT levels in the animals that received administration of miR-125b-5p. The HE staining of FIG. 20 shows significantly reduced hepatic injury in the group to which miR-125b-5p was administered. The lower GDH levels (FIG. 21), increased GSH/GSSG ratio and reduced serum levels of mtDNA (FIG. 23) in comparison to the control mice that had not received miR-125b-5p shows the activity of miR-125b-5p against a previous intoxication sufficient to induce acute liver failure.

EXAMPLE 6

Use of miR-125b-5p Against FAS-Induced Acute Liver Failure In Vivo

Figure 24:
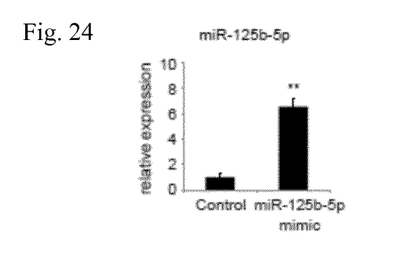
Figure 25:
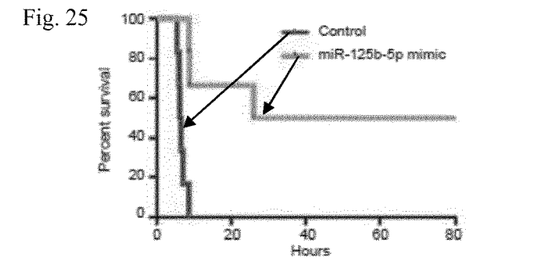

As a further example for the use of a compound having the nucleobase sequence of miR-125b-5p in the treatment of an intoxication causing acute liver failure, mice were injected with anti-CD95 antibody at a lethal dose that induces acute liver failure due to apoptosis and 1 h subsequently received 10 μg of the stabilized miR-125b-5p mimic or no compound (Control). FIG. 24 shows the analysed presence of the miR-125b-5p in the mice that had received the miR-125b-5p mimic (miR-125b-5p mimic) and in Control. The survival curve of FIG. 25 shows that the administration of miR-125b-5p drastically increases survival after injection of the anti-CD95 antibody for FAS-induced apoptosis.

Figure 26:
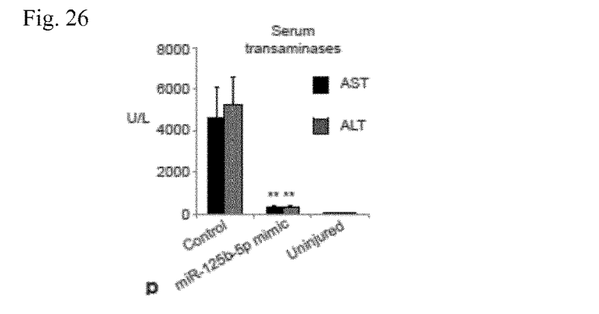

The serum levels of AST and ALT, depicted in FIG. 26, are reduced in the mice having received the miR-125b-5p when compared to the Control, but elevated compared to healthy mice (Uninjured).

Figure 27:
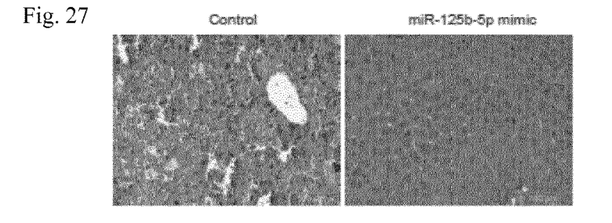

The HE staining of FIG. 27 indicates less apoptosis in liver tissue after 6 h following induction of acute liver failure by the anti-CD95 antibody in the mice having received the miR-125b-5p in comparison to significant apoptosis in the Control.

Figure 28:
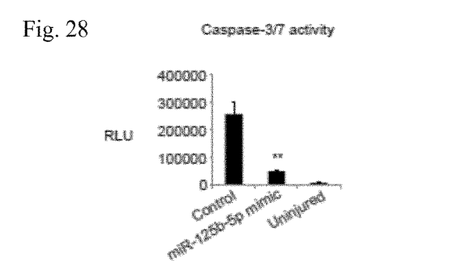

FIG. 28 shows lower caspase-3/7 activity in the mice that had received the miR-125b-5p mimic compared to Control, but higher activity compared to healthy (Uninjured) mice.

Figure 29:
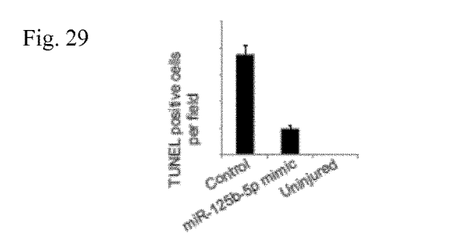

Decreased staining in TUNEL analysis in mice injected with miR-125b-5p compared to Control confirmed reduced apoptosis due to administration of miR-125b-5p following intoxication by anti-CD95 antibody injection. FIG. 29 shows the result of TUNEL analysis.

This example shows that administration of miR-125b-5p after intoxication sufficient to induce acute liver failure suppresses the acute liver failure and results in increased survival.

The invention claimed is:

1. A method for treating paracetamol-induced and/or FAS-induced acute liver failure, the method comprising administering within 4 days after intoxication a compound having a nucleobase sequence of SEQ ID NO: 1 (miR-125b-5p).

2. The method of claim 1, wherein the compound has a nucleobase sequence consisting of SEQ ID NO: 1.

3. The method of claim 1, wherein the nucleobase sequence is in the form of RNA, chemically stabilized RNA, chemically modified RNA and/or formulated as liposomes and/or nanoparticles.

4. The method of claim 1, wherein the acute liver failure is by hepatocyte apoptosis and/or necrosis.

5. The method of claim 1, wherein the compound is present in combination with at least one compound having a nucleobase sequence of miR-194-5p (SEQ ID NO: 2), miR-21-5p (SEQ ID NO: 3), let-7a-5p (SEQ ID NO: 4), miR-122-5p (SEQ ID NO: 5), miR-30c-5p (SEQ ID NO: 6), miR 193a-3p (SEQ ID NO: 7), miR-130a-3p (SEQ ID NO: 8), miR-29c-3p (SEQ ID NO: 9), miR-16-5p (SEQ ID NO: 10), and/or miR-23-3p (SEQ ID NO: 11).

6. The method of claim 1, wherein the nucleobase sequence is in the form of chemically modified RNA.

* * * * *

SEQUENCE LISTING

<160> NUMBER OF SEQ ID NOS: 11

<210> SEQ ID NO 1
<211> LENGTH: 22
<212> TYPE: RNA
<213> ORGANISM: Homo sapiens
<220> FEATURE:
<223> OTHER INFORMATION: miR-12b-5p

<400> SEQUENCE: 1
ucccugagac ccuaacuugu ga                                            22

<210> SEQ ID NO 2
<211> LENGTH: 22
<212> TYPE: RNA
<213> ORGANISM: Homo sapiens
<220> FEATURE:
<223> OTHER INFORMATION: miR-194-5p

<400> SEQUENCE: 2
uguaacagca acuccaugug ga                                            22

<210> SEQ ID NO 3
<211> LENGTH: 22
<212> TYPE: RNA
<213> ORGANISM: Homo sapiens
<220> FEATURE:
<223> OTHER INFORMATION: miR-21-5p

<400> SEQUENCE: 3

-continued uagcuuauca gacugauguu ga    22

<210> SEQ ID NO 4
<211> LENGTH: 22
<212> TYPE: RNA
<213> ORGANISM: Homo sapiens
<220> FEATURE:
<223> OTHER INFORMATION: let-7a-5p

<400> SEQUENCE: 4
ugagguagua gguuguauag uu    22

<210> SEQ ID NO 5
<211> LENGTH: 22
<212> TYPE: RNA
<213> ORGANISM: Homo sapiens
<220> FEATURE:
<223> OTHER INFORMATION: miR122-5p

<400> SEQUENCE: 5
uggaguguga caauggureguu ug    22

<210> SEQ ID NO 6
<211> LENGTH: 23
<212> TYPE: RNA
<213> ORGANISM: Homo sapiens
<220> FEATURE:
<223> OTHER INFORMATION: miR-30c-5p

<400> SEQUENCE: 6
uguaaacauc cuacacucuc agc    23

<210> SEQ ID NO 7
<211> LENGTH: 22
<212> TYPE: RNA
<213> ORGANISM: Homo sapiens
<220> FEATURE:
<223> OTHER INFORMATION: miR 193a-3p

<400> SEQUENCE: 7
aacuggccua caaagucccca gu    22

<210> SEQ ID NO 8
<211> LENGTH: 22
<212> TYPE: RNA
<213> ORGANISM: Homo sapiens
<220> FEATURE:
<223> OTHER INFORMATION: miR-130a-3p

<400> SEQUENCE: 8
cagugcaaug uuaaaagggc au    22

<210> SEQ ID NO 9
<211> LENGTH: 22
<212> TYPE: RNA
<213> ORGANISM: Homo sapiens
<220> FEATURE:
<223> OTHER INFORMATION: miR-29c-3p

<400> SEQUENCE: 9
uagcaccauu ugaaaucggu ua    22

<210> SEQ ID NO 10
<211> LENGTH: 22
<212> TYPE: RNA
<213> ORGANISM: Homo sapiens

```
<220> FEATURE:
<223> OTHER INFORMATION: miR-16-5p

<400> SEQUENCE: 10
uagcagcacg uaaauauugg cg                                            22

<210> SEQ ID NO 11
<211> LENGTH: 21
<212> TYPE: RNA
<213> ORGANISM: Homo sapiens
<220> FEATURE:
<223> OTHER INFORMATION: miR-23-3p

<400> SEQUENCE: 11
aucacauugc cagggauuuc c                                             21
```